US007597666B2

(12) United States Patent
Frinak et al.

(10) Patent No.: US 7,597,666 B2
(45) Date of Patent: Oct. 6, 2009

(54) ACCESS PRESSURE RATIO DEVICE AND TESTING METHOD

(76) Inventors: Stanley Frinak, 2799 W. Grand Blvd., CFP-543, Detroit, MI (US) 48202; Gerard Zasuwa, 2799 W. Grand Blvd., CFP-543, Detroit, MI (US) 48202; Jerry Yee, 2799 W. Grand Blvd., CFP-514, Detroit, MI (US) 48202; Anatole Besarab, 2799 W. Grand Blvd., CFP-511, Detroit, MI (US) 48202

( * ) Notice: Subject to any disclaimer, the term of this patent is extended or adjusted under 35 U.S.C. 154(b) by 314 days.

(21) Appl. No.: 10/516,389

(22) PCT Filed: Jul. 29, 2002

(86) PCT No.: PCT/US02/23958

§ 371 (c)(1), (2), (4) Date: Jun. 9, 2005

(87) PCT Pub. No.: WO03/011108

PCT Pub. Date: Feb. 13, 2003

(65) Prior Publication Data

US 2006/0272421 A1 Dec. 7, 2006

Related U.S. Application Data

(60) Provisional application No. 60/308,872, filed on Jul. 30, 2001.

(51) Int. Cl.
*A61M 37/00* (2006.01)
*A61B 5/02* (2006.01)
(52) U.S. Cl. .................. 600/485; 600/481; 600/486; 604/4.01; 604/5.01

(58) Field of Classification Search .................. 600/485, 600/481, 486; 604/4.01, 6.11, 6.14, 6.16, 604/65, 5.01, 19; 73/592; 210/739
See application file for complete search history.

(56) References Cited

U.S. PATENT DOCUMENTS

| 3,920,004 | A | * | 11/1975 | Nakayama | 600/493 |
|---|---|---|---|---|---|
| 4,303,068 | A | * | 12/1981 | Zelman | 604/6.09 |
| 4,466,804 | A | * | 8/1984 | Hino | 604/6.14 |
| 4,524,777 | A | * | 6/1985 | Kisioka et al. | 600/490 |
| 4,531,941 | A | * | 7/1985 | Zasuwa | 604/113 |
| 4,710,164 | A | * | 12/1987 | Levin et al. | 604/66 |
| 4,735,212 | A | * | 4/1988 | Cohen | 600/480 |
| 4,828,543 | A | * | 5/1989 | Weiss et al. | 604/6.09 |

(Continued)

FOREIGN PATENT DOCUMENTS

EP 240101 A2 10/1987

*Primary Examiner*—Patricia C Mallari
(74) *Attorney, Agent, or Firm*—Kohn and Associates PLLC

(57) ABSTRACT

The present invention discloses a detection device for detecting irregular intravascular pressure, the device including an analyzer for automatically analyzing intravascular pressure upstream of the suspected location of irregular blood flow, and a comparing device that correlates the recorded intravascular pressure to a standard whereby variation in the intravascular pressure during multiple tests is indicative of irregular blood flow. Also disclosed is a system for providing a warning of potential health problems due to irregular blood flow, the system including a detecting device as set forth above and a communicating device operatively connected to the detecting device for communicating a warning when the device indicates an irregularity of intravascular pressure during at least two uses of the device.

12 Claims, 12 Drawing Sheets

U.S. PATENT DOCUMENTS

| | | | |
|---|---|---|---|
| 5,453,576 A * | 9/1995 | Krivitski | 600/481 |
| 5,873,835 A * | 2/1999 | Hastings et al. | 600/488 |
| 6,090,048 A | 7/2000 | Hertz et al. | |
| 6,221,040 B1 | 4/2001 | Kleinekofort | |
| 6,228,033 B1 * | 5/2001 | Koobi et al. | 600/483 |
| 6,371,921 B1 * | 4/2002 | Caro et al. | 600/485 |
| 6,383,158 B1 * | 5/2002 | Utterberg et al. | 604/4.01 |
| 6,471,872 B2 * | 10/2002 | Kitaevich et al. | 210/739 |
| 6,514,225 B1 * | 2/2003 | Utterberg et al. | 604/6.16 |
| 6,517,508 B1 * | 2/2003 | Utterberg et al. | 604/4.01 |
| 6,579,241 B2 * | 6/2003 | Roeher | 600/485 |
| 6,595,942 B2 | 7/2003 | Kleinekofort | |
| 6,623,443 B1 * | 9/2003 | Polaschegg | 604/5.04 |
| 6,745,630 B2 | 6/2004 | Gross | |
| 6,755,801 B2 * | 6/2004 | Utterberg et al. | 604/4.01 |
| 7,172,570 B2 | 2/2007 | Cavalcanti et al. | |
| 2005/0096578 A1 | 5/2005 | Kleinekofort | |
| 2005/0203493 A1 | 9/2005 | Kuroda et al. | |
| 2006/0074369 A1 | 4/2006 | Oishi | |
| 2006/0157408 A1 | 7/2006 | Kuroda et al. | |
| 2007/0016084 A1 * | 1/2007 | Denault | 600/485 |

* cited by examiner

ACCESS PRESSURE RATIO DEVICE AND TESTING METHOD

CROSS-REFERENCE TO RELATED APPLICATIONS

This patent application is a National Phase Concerning a Filing Under 35 U.S.C. 371, claiming the benefit of priority of POT/US02/23958, filed Jul. 29, 2002, which claims the benefit of priority of U.S Provisional Patent Application Ser. No. 60/308,872, filed Jul. 30, 2001, all of which are incorporated herein by reference.

BACKGROUND OF THE INVENTION

1. Field of the Invention

The present invention relates to devices and methods for detecting failure in a system based on pressure measurements. More specifically, the present invention relates to systems and methods for use in industrial and medical applications.

2. Description of Related Art

Proper functioning of the vascular system is essential for the health and fitness of living organisms. The vascular system carries essential nutrients and blood gases to all living tissues and removes waste products for excretion. The vasculature is divided into different regions depending on the organ systems served. If vessels feeding a specific organ or group of organs are compromised, the organs and tissues supplied by those vessels are deleteriously affected and can even fail completely.

Vessels, especially various types of arteries, not only transmit fluid to various locations, but are also active in responding to pressure changes during the cardiac cycle. With each contraction of the left ventricle of the heart during systole, blood is pumped through the aorta and then distributed throughout the body. Many arteries contain elastic membranes in their walls that assist in expansion of the vessel during systole. These elastic membranes also function in smoothing pulsatile blood flow throughout the vascular system. The vessel walls of such arteries often rebound following passage of the systolic pressure waveform.

In autoregulation, cerebral blood vessels maintain constant cerebral blood flow by either constricting or dilating over a certain mean arterial blood pressure range so that constant oxygen delivery is maintained to the brain. Vascular failure occurs when the pressure drops too low and the oxygen delivery starts to fall. If the blood pressure gets too high and the vessels can no longer constrict to limit flow, then hyperemia breakthrough or loss of autoregulation can occur. Both of these conditions are pathologic states, and have been described in the literature in terms of mean arterial pressure and cerebral blood flow velocity, but there are others that cannot be explained based on that model. The failure of the model is that it relies upon systemic blood pressure. The pressure of blood in the brain itself is not being measured directly. The resultant pressure curve has an S-shaped curve.

The force applied to the blood from each heartbeat is what drives the blood forward. In physics, force is equivalent to mass times acceleration. But when blood is examined on a beat-to-beat variation, each heartbeat delivers about the same mass of blood, unless there is severe loss of blood or a very irregular heart rhythm. Therefore, as a first approximation, the force of flow on the blood at that particular moment is directly proportional to its acceleration.

Diseased blood vessels lose the ability to stretch. The elasticity or stretch of the blood vessel is very critical to maintaining pulsatile flow. When a muscle is stretched, it is not a passive relaxation. There is a chemical reaction that happens within the muscle itself that causes a micro-contracture to increase the constriction, so that when a bolus of blood comes through with each heartbeat, it stretches the blood vessel wall, but the blood vessel then contracts back and gives the kick forward to maintain flow over such a large surface area. This generates a ripple of waves, starting in the large vessel of the aorta and working its way through the rest of the vessels. As vessels become diseased, they lose the ability to maintain this type of pulsatile flow.

Further, if vessels are compromised due to various factors such as narrowing or stenosis of the vessel lumen, blood flow becomes abnormal. If narrowing of a vessel is extensive, turbulent flow can occur at the stenosis resulting in damage to the vessel. In addition, blood cannot flow adequately past the point of stenosis, thereby injuring tissues distal to the stenosis. While such vascular injuries can occur anywhere throughout the body, the coronary and cerebral vascular beds are of supreme importance for survival and well-being of the organism. For example, narrowing of the coronary vessels supplying the heart can decrease cardiovascular function and decrease blood flow to the myocardium, leading to a heart attack. Such episodes can result in significant reduction in cardiac function and death.

Abnormalities in the cerebral vessels can prevent adequate blood flow to neural tissue, resulting in transient ischemic attacks (TIAs), migraines, and stroke. The blood vessels that supply the brain are derived from the internal carotid arteries and the vertebral arteries. These vessels and their branches anastomose through the great arterial circle, also known as the Circle of Willis. From this Circle arise the anterior, middle and posterior cerebral arteries. Other arteries such as the anterior communicating artery and the posterior communicating artery provide routes of collateral flow through the great arterial circle. The vertebral arteries join to form the basilar artery, which itself supplies arterial branches to the cerebellum, brain stem and other brain regions. A blockage of blood flow within the anterior cerebral artery, the posterior cerebral artery, the middle cerebral artery, or any of the other arteries distal to the great arterior circle results in compromised blood flow to the neural tissue supplied by that artery. Since neural tissue cannot survive without normal, constant levels of glucose and oxygen within the blood and provided to neurons by glial cells, blockage of blood flow in any of these vessels leads to death of the nervous tissue supplied by that vessel.

Strokes result from blockage of blood flow in cerebral vessels due to constriction of the vessel resulting from an embolus or stenosis. Strokes can also arise from tearing of the vessel wall due to any number of circumstances. Accordingly, a blockage can result in ischemic stroke depriving neural tissue distal to the blockage of oxygen and glucose. A tearing or rupture of the vessel can result in bleeding into the brain, also known as a hemorrhagic stroke. Intracranial bleeding exerts deleterious effects on surrounding tissue due to increased intracranial pressure and direct exposure of neurons to blood. Regardless of the cause, stroke is a major cause of illness and death. Stroke is the leading cause of death in women and kills more women than breast cancer.

Currently, more than three-quarters of a million people in the United States experience a stroke each year, and more than twenty-five percent of these individuals die. Approximately one-third of individuals suffering their first stroke die within the following year. Furthermore, about one-third of all survivors of a first stroke experience additional strokes within the next three years.

In addition to its terminal aspect, stroke is a leading cause of disability in the adult population. Such disability can lead to permanent impairment and decreased function in any part of the body. Paralysis of various muscle groups innervated by neurons affected by the stroke can lead to confinement to a wheelchair, and muscular plasticity and rigidity. Strokes can leave many patients with little or no ability to communicate either orally or by written means. Often, stroke patients are unable to think clearly and have difficulties naming objects, interacting well with other individuals, and generally functioning within society.

Despite the tremendous risk of stroke, there are presently no convenient and accurate methods to access vascular health. Many methods rely on invasive procedures, such as arteriograms, to determine whether vascular stenosis is occurring. These invasive techniques are often not ordered until the patient becomes symptomatic. For example, carotid arteriograms can be ordered following a physical examination pursuant to the appearance of a clinical symptom. Performing an arteriogram is not without risks due to the introduction of dye materials into the vascular system that can cause allergic responses. Arteriograms also use catheters that can damage the vascular wall and dislodge intraluminal plaque, which can cause an embolic stroke at a downstream site. It would therefore be useful to develop a noninvasive or limited invasive procedure for assessing vascular health.

Further, in the field of hemodialysis and other techniques where blood is removed from a patient for processing and then returned, it is important to periodically assess the blood flow rate through an arteriovenous fistula, graft, or catheter to monitor the onset of stenosis. This is often accomplished by the reading of access pressures through the venous and arterial access needles. Early detection of stenosis associated with the placement of a fistula, graft, implantable port, or a catheter can permit low cost repairs to be made. On the other hand, if these problems are ignored or not detected, the cost of the revision or replacement of the fistula, graft, implantable port, or catheter can be very high and burdensome to the patient.

As disclosed in U.S. Pat. No. 5,454,374, to Omachi, access pressures can be determined through volumetric manipulations involving the determination of a pressure head height of blood in a visual manner. (The blood line going to the dialysis machine is used to measure pressure and the problem is one of determining the height between the transducer and the patient's access site.)

It would be desirable to directly read the access pressure through an access needle, before a blood tubing set is attached. The blood tubing set transports blood between the patient's access needles the and the membrane dialyzer. When reading the access pressure directly from the access needles it is important to isolate the sterile access needle set from the connected unsterile pressure gauge. Also, there is a need to dampen the pressure pulse that is naturally provided by the pulsatile flow of blood in the patient, to provide a mean pressure reading that is not strongly subject to inaccuracies due to head height variations. Ideally, the reading should be taken at about the level of the heart.

There is a need for a system that facilitates the ability of a health care provider to conveniently and rapidly transmit vascular flow data parameters obtained from a patient to a location where consistent, reproducible analysis is performed. The results of the analysis can then be transmitted to the healthcare provider to facilitate accurate diagnosis or prognosis of a patient, to recommend treatment options, and to discuss the ramifications of those treatment options with the patient.

There is also a need for a system that enables health care providers to measure the rate and type of developing vascular disease, and to recommend interventions that prevent, minimize, stabilize, or reverse the disease.

There is a further need for a system that enables health care providers to predict the vascular reaction to a proposed therapeutic intervention, and to modify the proposed therapeutic intervention if a deleterious or adverse vascular response is anticipated. Physicians often prescribe therapeutic substances for patients with conditions related to the cardiovascular system that can affect vascular health. For example, hypertensive patients can be prescribed beta-blockers with the intent of lowering blood pressure, thereby decreasing the probability of a heart attack. Patients frequently receive more than one therapeutic substance for their condition or conditions. The potential interaction of therapeutic substances at a variety of biological targets, such as blood vessels, is often poorly understood. Therefore, a noninvasive method that can be used to assess the vascular effects of a substance, such as a therapeutic substance or a combination of therapeutic substances, is needed. A clearer understanding of the vascular effects of one or more substances on blood vessels can deter prescriptions of substances with undesirable and potentially lethal effects, such as stroke, vasospasm and heart attack. It would be useful to develop a system and method for repeatedly assessing vascular health in a patient population during a clinical trial.

Furthermore, a system and method that can provide assessment of the vascular health of an individual is needed. Also needed is a system and method that can be used routinely to assess vascular health, such as during periodic physical examinations. This system and method preferably is noninvasive and provides information concerning the compliance and elasticity of a vessel. Also needed is a system and method that can be used to rapidly assess the vascular health of an individual. Such systems and methods can be available for use in routine physical examinations, and especially in the emergency room, an intensive care unit, or in a neurological clinic. It would therefore be useful to develop a system and method that can be applied in a longitudinal manner for each individual so that the vascular health of the individual can be assessed over time. In this manner, a problem or a disease process can be detected before the appearance of a major cerebral vascular accident or stroke.

SUMMARY OF THE INVENTION

The present invention discloses a detection device for detecting irregular intravascular pressure, the device including an analyzer for automatically analyzing blood pressure upstream of the suspected location of irregular blood flow, and a comparator device that correlates the intravascular pressure to a standard, whereby variation in the intravascular pressure during multiple tests is indicative of irregular blood flow. Also disclosed is a system for providing a warning of potential health problems due to irregular intravascular pressure, the system including a detecting device as set forth above and a communicating device operatively connected to the detecting device for communicating a warning when the device indicates an irregularity of blood pressure during at least two uses of the device.

BRIEF DESCRIPTION OF THE DRAWINGS

Other advantages of the present invention can be readily appreciated as the same becomes better understood by reference to the following detailed description when considered in connection with the accompanying drawings, wherein.

DETAILED DESCRIPTION OF THE INVENTION

Figure 1:
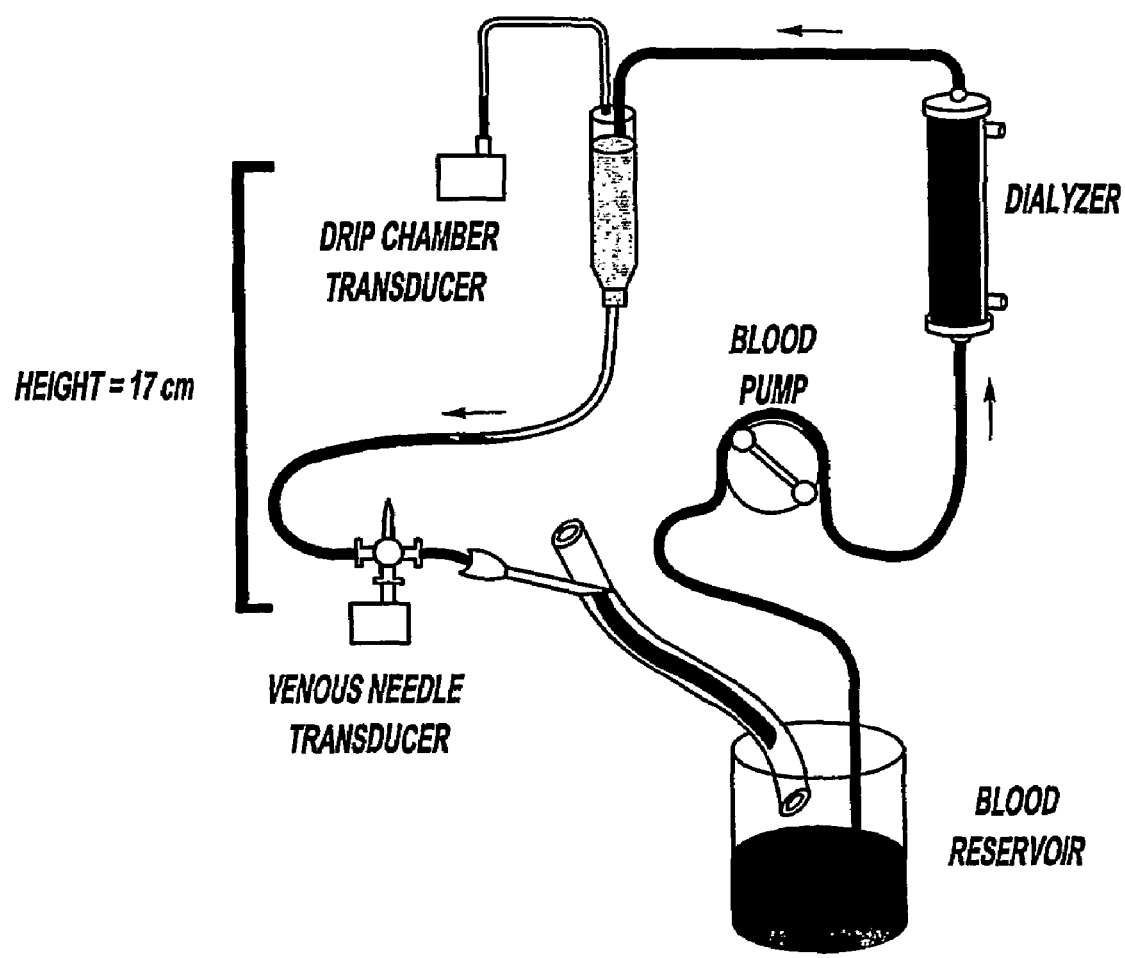
FIG. 1 shows the dialysis circuit used to determine the relationship between blood flow and hemodialysis machine venous drip chamber pressure with hematocrit varied from 38.4% to 18.2%.

Generally, the present invention provides a detection device and method for detecting variations in intravascular pressure that indicate irregular blood flow. The device includes an analyzer for automatically analyzing intravascular pressure upstream of the suspected location of irregular blood flow and comparing the intravascular pressure to a standard, whereby variations in the intravascular pressure during multiple tests is indicative of a blood flow restriction.

The "detection device" as disclosed herein is intended to include, but is not limited to, any device that is able to detect variations in intravascular pressure that indicate irregular blood flow. Preferably, the intravascular pressure is venous pressure that is upstream of the suspected area or location of a blood flow restriction. An example of such a device is a hemodialysis machine.

The "analyzer device" as used herein is intended to include a device that is capable of automatically analyzing the intravascular pressure. Such an analyzer device can be computer-driven. For example, the analyzer can include a device that is associated with a hemodialysis machine, such that it automatically assesses intravascular pressure during hemodialysis. The analyzer can then equate and compare the intravascular pressure to a standard. An equation is used that estimates pressure inside a blood access site and is then used to detect irregular blood flow. This equation is preferably an algorithm that calculates the ratio between venous blood pressure and mean arterial pressure.

The term "variation" is intended to include an increase or decrease in the measured intravascular pressure. Any deviation from the standard can be indicative of a problem. Depending upon whether there is an increase or decrease in intravascular pressure, the detection of the deviation helps determine what the problem is at the access site. For example, if there is an increase in intravascular pressure, the problem potentially is something that blocks normal blood flow downstream of the measurement site. The blockage represents a narrowing of a blood vessel that increases the risk for an access failure, a stroke, or a heart attack. If there is a decrease in intravascular pressure, this is indicative of a blockage of normal blood flow upstream of the measurement site.

The term "communication device" as used herein is intended to include a device operably connected to the detecting device for communicating a warning when the detecting device indicates an irregularity of blood pressure of at least two uses of said device. The communicating device can be selected from, but is not limited to, electronic communications, a facsimile, a telephone, a cable modem, and a T1 connection.

The term "algorithm" as used herein is intended to encompass any computation that enables an individual to ascertain the information necessary for detecting irregular intravascular pressure. The algorithm is preferably computer driven and follows the general function shown in FIGS. 7A through D. The algorithm can be used as part of an integrated circuit. This circuit enables the algorithm to be more easily incorporated into a dialysis machine. The circuit can be created using technology known to those with skill in the art.

The device of the present invention includes a detection device for detecting irregular intravascular pressure, the device including an analyzer for automatically monitoring intravascular pressure upstream of the suspected location of irregular blood flow, and a device for comparing intravascular pressure to a standard, whereby variation in the intravascular pressure during multiple tests is indicative of irregular blood flow. As disclosed above, in the preferred embodiment, the device is affixed to a hemodialysis machine. The analyzer is a computer-driven device and preferably, includes an algorithm that analyzes intravascular pressure, hemodialysis venous access pressure, and blood pump flow data to identify patients at-risk for access dysfunction, either for thrombosis requiring percutaneous transluminal angioplasty, or surgery to maintain access patency.

The device can also be included as a portion of a system that is used for monitoring individuals for potential health problems due to irregular blood flow. The system includes a detecting device, as set forth above, and a communicating device operatively connected to the detecting device for communicating a warning when the device indicates an irregularity of blood pressure or an indication that the machine is not affixed properly. Preferably, the system monitors an individual during at least two uses of the device. The warning can be an audible warning or other similar signal. Alternatively, the warning can actually be a communication to a health care professional. The latter warning can be a warning that is transmitted via the Internet to a health care professional. Examples of such communication devices can include, but are not limited to electronic communications, facsimile, telephone, cable modem, and T1 connection.

Alternatively, the device can be included as part of a hand-held device. In this embodiment, the device includes a replacement of the pressure gauge with a hand-held microprocessor controlled device that measures and records the pressure measurements. An algorithm in the device calculates the average pressure over a predetermined sampling period. The device also contains a computer database to recall individual patient information and to record current pressure measurements in the patient's database record. Data from the device can be transferred via a communication port to a larger computer system with a more extensive patient database.

Generally, the present invention provides a method and device for monitoring and/or detecting failure in a system based on pressure measurements. The present invention has numerous applications this can include, but is not limited to, mechanical, chemical, and biological arts. For instance, in chemical processes, the present invention is useful where pressure changes are indicative of system failure. Additionally, the method and device of the present invention can be used for detecting any variation in blood pressure and forwarding via the communicating device a warning regarding this variation. The device and method therefore can be used in detecting potential access failure, risk of stroke, risk of heart attack, risk of stenosis, and risk of aneurysm.

More specifically, failure or assessment of system failure is predicted, thereby allowing for opportunity to adjust or repair the system prior to failure thereof. Thus, a security system preventing failure is further provided herein. This is acutely critical where failure can be tragic, when combined with a system for repairing the failure. The two systems can be operatively connected to automate detection and repair. For example, water feed systems generally work along a pressure gradient. A drop in pressure can cause contamination of the system. The present invention is used to detect a drop in pressure of the magnitude resulting in failure. A repair system is then activated to give notice of the impending failure. Additionally, the repair system can increase pressure, thereby preventing failure.

Preferably, the present invention is for use in the noninvasive monitoring of vascular grafts. The present invention provides a method or an algorithm that can furnish a warning to the dialysis center that a patient's vascular access graft is likely to fail within a certain period of time following the warning signal. Preferably, the present invention provides at least a three-month warning of such failure.

Alternatively, the present invention can be used in various other applications. For instance, it can be used to determine the pressure in the venous line returning to the patient to develop an alarm system. The alarm can function in a number of manners. For instance, the alarm can provide a warning if the patient's needle came out of the access. Thus, the venous drip chamber pressure is equal to or close to venous drip chamber at zero access pressure for an alarm to occur. Currently, dialysis machines cannot detect an opening of the venous return line and incidents of severe bleeding have been reported when the venous needle has come out of the access site during dialysis. The algorithm for the present invention can be utilized as an alarm system in any device that transports blood from a patient to an extracorporeal circuit and returns the blood to the patient. The algorithm determines the alarm level based on the rate of fluid flow through the device and the physical properties of the fluid transported through the device. The algorithm allows the alarm level to vary with the rate of fluid flow through the device. The present device can be utilized as an alarm in plasmapheresis, heart lung machines and any extracorporeal blood treatment or infusion technology circuits. Alarm systems base on the present device are not limited to medical applications but can be developed for any fluid transporting device. Alarm levels can be set at any pressure value that provides safe operation of the device.

Additionally, the present invention can be applied to monitor the arterial line supplying the dialysis machine. A significant increase in the negative pressure created by the dialysis machine blood pump removing blood from the patient can be used to indicate the presence of an arterial stenosis or an obstruction of the arterial line. Further, the present invention can be utilized to describe the relationship between blood flow, pressure, and hematocrit in any type of system that removes blood from a patient and returns the same blood to the patient. Thus, it can be used in conjunction with a heart-lung machine to determine alarm parameters for blood withdrawal and reinfusion.

The present device can be used to monitor any type of patient blood access site for increased blood pressure and subsequently reduced blood flow. The types of blood access sites that can be monitored include, but are not limited to, fistulas, grafts, catheters, or any type of permanent blood access port. In catheters and permanent blood access ports the plastic materials used to construct the devices become coated with layers of protein and fibrous substances that reduce the internal diameter of the blood pathway or these devices may induce the formation of a vascular stenosis downstream of the implantation site. Any reduction in internal diameter of the blood pathway that results in an increase in pressure upstream of the catheter or permanent blood access port can be detected by the algorithm in the present device and a warning can be issue once an appropriate alarm level is exceeded.

The present invention can be used with intravenous infusion systems to determine the pressure profile for fluid infusion through a known tubing set and needle. A significant increase in the infusion pressure at the specified fluid viscosity and flow rate can be used to determine alarm conditions and prevent infusion of fluid into the tissue if the needle is not inside the lumen of the vein. Further, any industrial system that requires regulation of infusion pressure can utilize the present invention to develop a monitoring system based on the analysis of infusion pressure.

Hemodialysis access monitoring programs that measure access flow or intra-access pressure have been developed for early detection of evolving stenotic lesions (1-8). Studies have shown that early detection of stenotic lesions followed by timely corrective procedures reduces the thrombosis rate and improves hemodialysis access survival (1,3,9,10). Access monitoring programs are costly because they require equipment, personnel, data storage, and analysis. The method of the present invention is an inexpensive technique known as the venous access pressure ratio test (VAPRT), and obviates these encumbrances.

During hemodialysis, blood is drawn from the vascular access through the arterial needle by the hemodialysis machine blood pump. After passage through the dialyzer, the blood traverses the venous drip chamber and returns to the access through the venous needle. The pressure required to infuse blood back into the access through the venous tubing and access needle and to overcome the pressure within the access is recorded as the venous drip chamber pressure (VDP). One component of VDP is the access pressure at the venous needle site (hereafter, termed "venous access pressure" (VAP)). Another component of VDP is the combined pressure required to overcome the resistance to flow through the tubing distal to the drip chamber (low) and through the venous return needle (high). VDP is also a function of needle size, tubing length and blood viscosity, represented by hematocrit. If the venous pressure within an access at the needle site is 0 mmHg, VDP can be defined as $VDP_0$, i.e., the venous drip chamber pressure when the access pressure is zero. Consequently, $VDP_0$ can be calculated for a given hemodialysis machine, tubing set, and needle size when the blood flow rate and hematocrit are measured. Once $VDP_0$ is determined, VAP can be calculated from the measured VDP.

$$VAP = VDP - VDP_0 \quad \text{Equation (1)}$$

An elevation of VAP indicates stenosis in the venous outflow of the access and is associated with increased access failure probability (6,8,11,14). To normalize variations in VAP attributed to changes in mean arterial pressure (MAP), the venous access pressure ratio (VAPR) is calculated by dividing VAP by MAP.

$$VAPR = VAP/MAP \quad \text{Equation (2)}$$

The data that yields the determination of $VDP_0$ is contained within a central database repository that holds dialysis laboratory data and parameters acquired from hemodialysis machines that directly communicate with computers in the dialysis units. The VAPRT algorithm utilizes an empirical formula to calculate VAP from a dynamic measurement of VDP obtained at treatment and digitally recorded. The VAPRT algorithm analyzes monthly VAPR values and identifies individuals with consistently elevated intra-access pressures at risk for access failure. To eliminate treatment errors such as needle reversal or suboptimal needle placement that cause elevated VDP, an abnormal VAPRT was operationally defined as VAPR>0.55 at three treatments.

Analysis of the data for the hemodialysis machine circuit yielded the following second order polynomial equation, henceforth referred to as equation (3):

$$VDP_0 = 0.00042 \cdot Qb^2 + (0.62116 \cdot Hct^2 + 0.01203 \cdot Hct + 0.12754) \cdot Qb - 17.32509 \quad \text{Equation (3)}$$

Equation (3) can be used to calculate $VDP_0$ for any Qb at known Hct. For example, at Qb=500 ml/min and Hct 18.2%, $VDP_0$ is 163 mmHg and increases to 200 mmHg when Hct=38.4%. VAP can be calculated from VDP recorded at HD by Equation (1) and VAPR is calculated by Equation (2). At Hct 38.4%, Qb 500 ml/min, VDP 265 mmHg, $VDP_0$ 200 mmHg, and MAP 100 mmHg, VAPR=0.65=(265−200)/100. In the case where blood flow (Qb) is equal to zero in equation (3), the following occurs:

$$VDP_0 = 0 + 0 - 17.32509 = -17.32509$$

Venous access pressure (VAP) is then calculated using equation (1).

$$VAP = VDP - VDP_0 \quad VAP = VDP - (-17.32509)$$
$$VAP = VDP + 17.32509$$

The constant (−17.32509) is determined by the dialysis machine type and the level of the patients access site. Clinical studies have shown that the venous drip chamber pressure recorded by the machine and corrected for the height difference between the drip chamber transducer the patient's access gives an accurate value for venous access pressure (8,22). The algorithm can therefore be incorporated into the dialysis machine. The dialysis machine therefore automatically records the readings. Additionally, a sensor can be placed on the hemodialysis machine to determine the height difference between the venous drip chamber transducer and the level of the patient's access site.

The VAPRT relies on a nonlinear regression formula to calculate $VDP_0$ for specific hemodialysis blood tubing set and access needle when the patient's hemodialysis blood pump flow (Qb) and hematocrit are known. The formula was developed from data analysis obtained during in vitro sham hemodialysis. FIG. 1 shows a diagram of the experimental hemodialysis system. The dialysis machine (Fresenius 2008H, Lexington, Mass., USA) blood pump was calibrated prior to experiments using the standard maintenance procedure. The exact flow was not measured during the in vitro experiment as the intention a priori was to design a monitoring system that utilized routine dialysis data obtained from each dialysis treatment. The reservoir is filled with 500 ml of human whole blood obtained from the hospital blood bank. The blood pump transports blood from a reservoir through the dialyzer and the venous drip chamber and then to a 15 gauge, 1-inch backeye access needle. The venous access needle is inserted into a section of large-bore tubing that is open at both ends. One end of the tubing returns blood to the reservoir and the other end is elevated to prevent blood from escaping. This section of the circuit is not designed to simulate an actual access, but to avoid any resistance to flow at the tip of the venous access needle that can be recorded as an increase in VDP. The access needle is positioned 17 cm below the venous drip chamber transducer to simulate the average location of an angioaccess relative to the transducer during a typical hemodialysis treatment. The drip chamber transducer monitors the pressure created by the blood flowing through the circuit. $VDP_0$ readings are obtained directly from the hemodialysis machine. A sample of blood is obtained for hematocrit determination from the reservoir. $VDP_0$ is recorded as Qb is increased from 0 to 600 ml/mm in 50 ml/mm increments. A separate transducer, placed directly behind the access needle, measures the pressure created by the access needle's intrinsic resistance. The blood is then diluted with matched human plasma to lower hematocrit by approximately 4%. Blood is permitted to circulate at 500 ml/mm for 5 minutes to ensure uniform mixing with the additional plasma before the next sample is obtained for hematocrit measurement. $VDP_0$ measurements are repeated for Qb from 0 to 600 ml/mm. The circulated blood is diluted five times, reducing the original hematocrit by approximately 20 percentage points. $VDP_0$ measurements were conducted at each of the five dilutions.

The test monitors for a persistent elevation of the VAPR to identify an access that requires additional evaluation. The algorithm calculates VAPR from VDP and blood pump flow data that is routinely collected during hemodialysis and stored in a computer database. The algorithm determines whether a persistent increase in VAPR is present during sequential treatments.

To limit variability intrinsic to differences in needle gauge, patients with less than 48 hemodialysis treatments were eliminated from analysis because a smaller gauge needle is frequently used when initially cannulating a new or poorly developed angioaccess. The program extracts the most recent hematocrit and individual treatment data from the computer database and analyzes data for those patients who receive treatments via a graft. The VAPR is calculated each time the blood pressure is measured during hemodialysis, given the following criteria: Qb≧200 ml/mm, VDP≧20 mmHg and MAP≧75 mmHg. Data from the last hour of hemodialysis is excluded to eliminate the effect of ultrafiltration on hematocrit (elevated blood viscosity), blood pressure, and changes in systemic and vascular access resistances. The algorithm then calculates the mean VAPR for each hemodialysis treatment using all available data. In the majority of cases three or four measurements are available. Patients with <10 hemodialysis treatments during a month were excluded. The VAPRT is considered positive when, starting with the eighth treatment of the month; the program determines that the VAPR exceeds the specified cutoff value during three consecutive treatments.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations that become evident as a result of the teaching provided herein.

EXAMPLES

Example 1

Criterion for the Venous Access Pressure Ratio Test

To determine the VAPR cutoff value most predictive of access failure, test data and follow up data were analyzed from 117 patients with grafts who received hemodialysis treatment at three hemodialysis facilities during January 1999. VAPR in these patients were correlated with the presence or development of access dysfunction, stenosis requiring intervention by angioplasty or surgical revision to maintain access patency, or the occurrence of thrombosis within the six months of follow up observation. A six month observation period was selected because data reported showed that primary unassisted patency for grafts at six months is 64% and secondary assisted patency is 70% at six months, which is in accordance with data from Sparks (15) showing a primary patency for grafts of 64% at a median of seven months. The data from these studies indicates that in any six month period 30 to 36% of all grafts can fail. The VAPRT is being used to try and identify grafts in this group before they fail.

A receiver operator curve (ROC) for VAPRT was constructed with cutoff ratios of 0.2, 0.3, 0.4, 0.45, 0.5, 0.55, 0.6 and 0.8 while other test parameters were held constant. The respective sensitivities and specificities were calculated at each VAPR cutoff level. Areas under the receiver operator (ROC) curves were calculated using Mathcad Plus 6.0 (MathSoft Inc., Cambridge, Mass., USA). Clinical results were analyzed with StatView for Windows v. 5.0 (SAS Institute, Inc., Cary, N.C., USA) and DeltaGraph 4.0 (SPSS, Inc., Chicago, Ill., U.S.A.). Grouping variables for unpaired t-tests were true positive (TP; test predicted intervention or access clotting), true negative (TN; test correctly predicted the absence of an access event), false positive (FP; test falsely predicted an access event would have occurred) and false negative (FN; test falsely predicted that an access event would not occur). The hypothesized difference between groups for all comparisons was zero.

Clinical Application of Venous Access Pressure Ratio Test

A total of 359 VAPRT were acquired from ESRD patients in three Greenfield Health System hemodialysis units over a three month interval following the determination of the optimal VAPR=0.55. The same population's data was retrospectively analyzed from January (n=112), February (n=113) and March (n=134) of 1999. Medical records were examined to identify those individuals who required intervention for an access event, defined as an obviously low access flow (<250 ml/mm), an inability to provide adequate dialysis within the predetermined treatment time or surgical or angioplasty intervention to maintain access patency, from stenosis or thrombosis.

Results

In vitro Modeling of $VAP_0$

Derivation of the Mathematical Model

Figure 2:
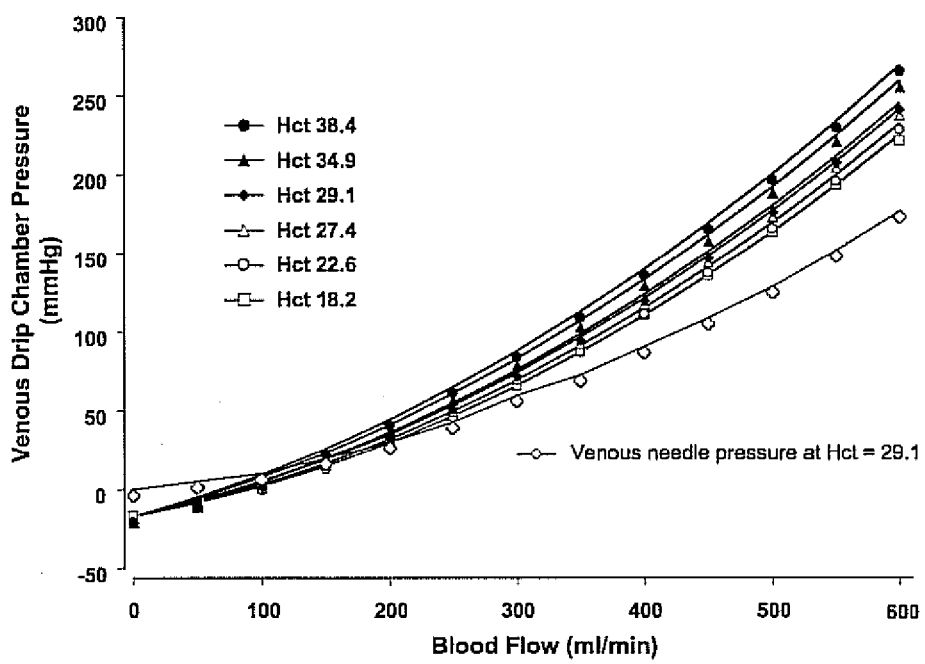
FIG. 2 shows the venous drip chamber pressure versus blood flow in a hemodialysis machine blood circuit for a range of hematocrit values. Included in the figure is a single curve showing venous needle pressure at a hematocrit of 29.1%, venous needle pressure is 0 mmHg when Qb=0 because the transducer and the venous needle are at the same height; venous drip chamber pressure is approximately −17 mmHg when Qb=0 because the venous needle is 17 centimeters below the height of the drip chamber transducer.

Results of the sham dialysis study are shown in FIG. 2. Mathematical modeling of $VDP_0$ data is shown in FIG. 2. The data in FIG. 2 was analyzed by fitting each individual curve with an equation of the form:

$$VDP_0 = A \cdot Qb^2 + B \cdot Qb + C \qquad \text{Equation (1a)}$$

The constant C represents the value of VDP when Qb=0 and the average value of −17.325 mmHg was used during further analysis of the data. Because coefficient A varied minimally from 0.0004232 to 0.0004327, an increase of only 1.5 mmHg in VDPQ at Qb=400, a mean value of 0.00042329 was used. Coefficient B varied the most with hematocrit from 0.145289 to 0.231968. The raw data was then fit with Equation (2a).

$$VDP_0 = 0.00042329 \cdot Qb^2 + B \cdot Qb - 17.325 \qquad \text{Equation (2a)}$$

Figure 6:
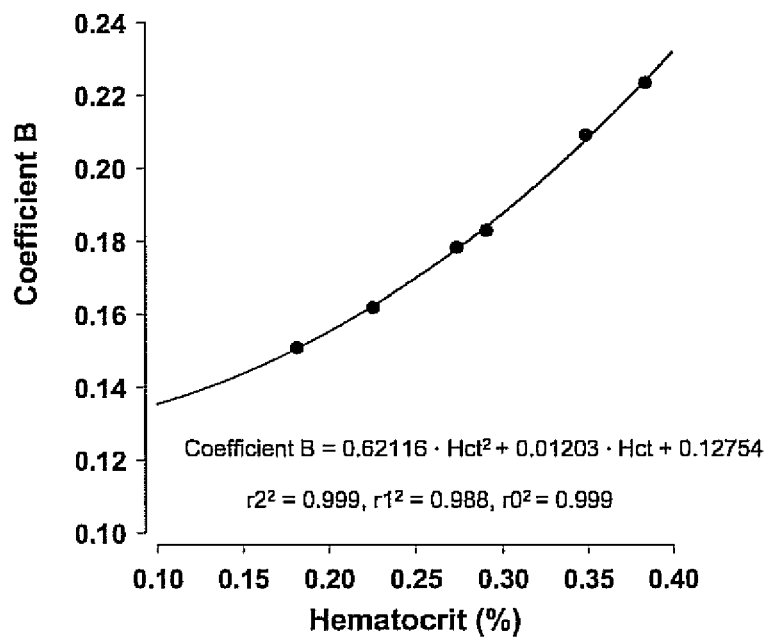
FIG. 6 is a graph showing the relationship between coefficient B in the equation for venous drip chamber pressure with zero venous access pressure $VDP_0=0.00042329 \cdot Qb^2+B \cdot Qb$ 17.325 and hematocrit (Hct).
Figure 8:
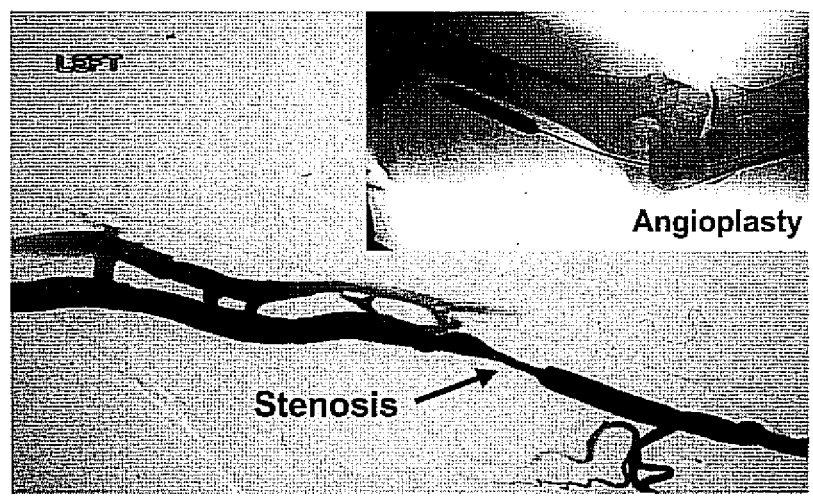
FIG. 8 is a photograph of a percutaneous transluminal angioplasty.
Figure 7:
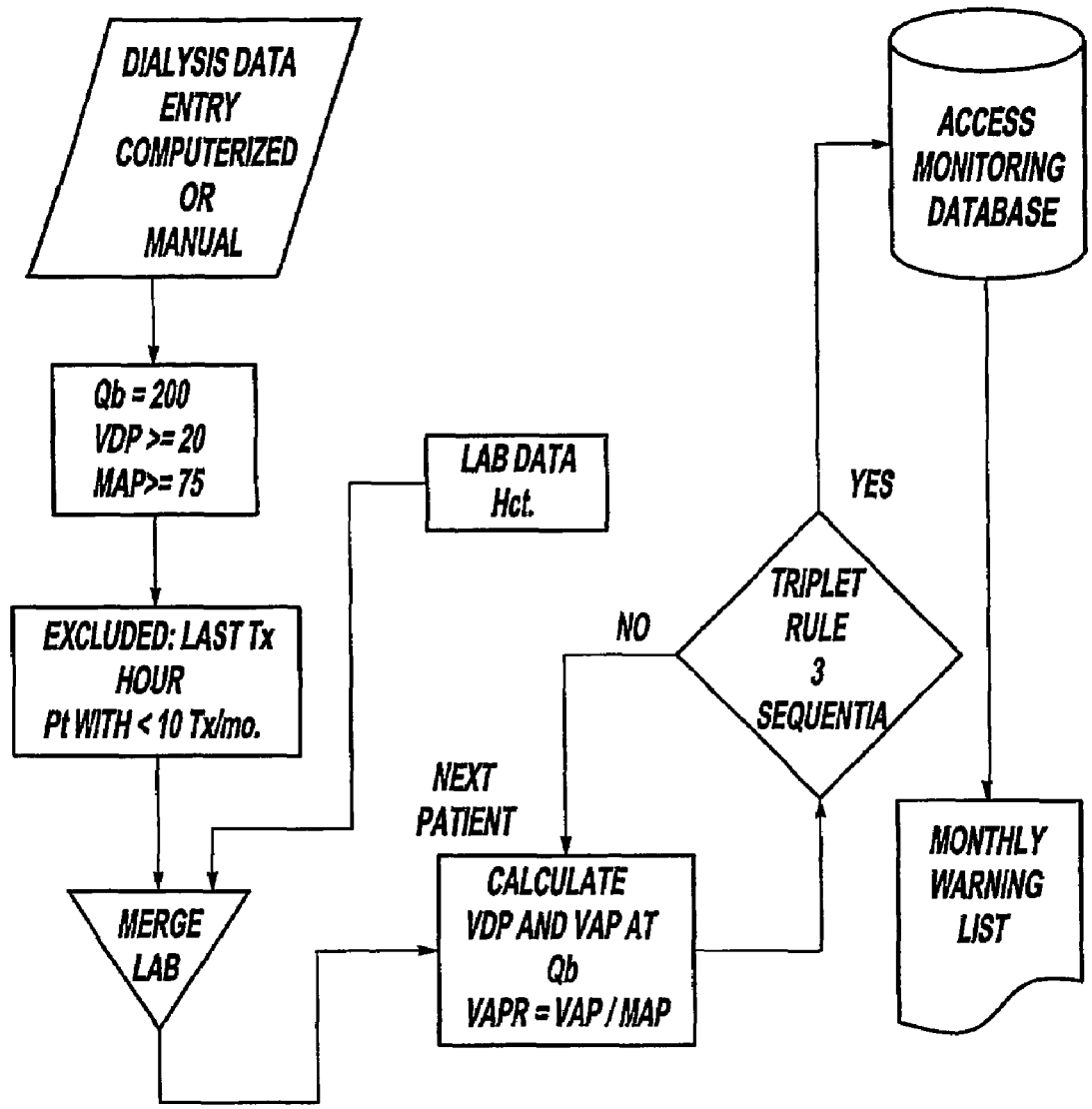
FIG. 7 is a flow chart depicting the inner workings of the device of the present invention.
Figure 7A:
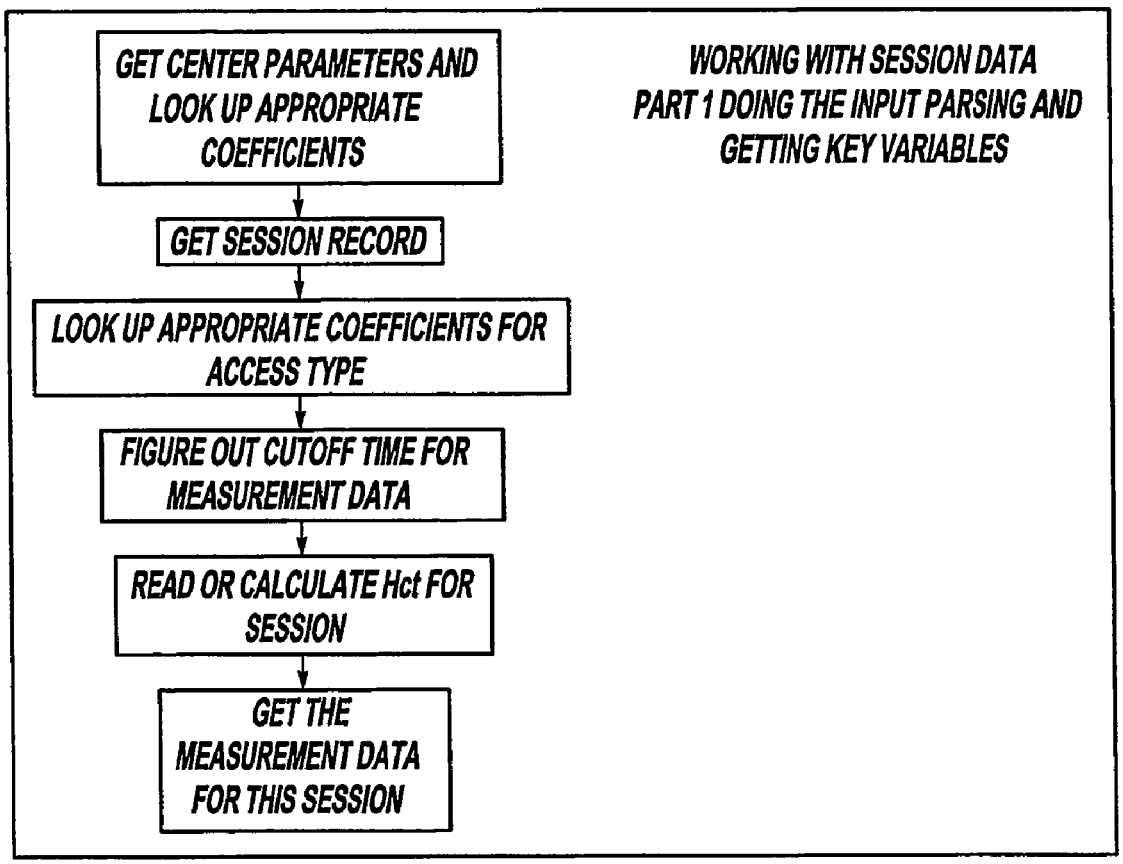
Figure 7B:
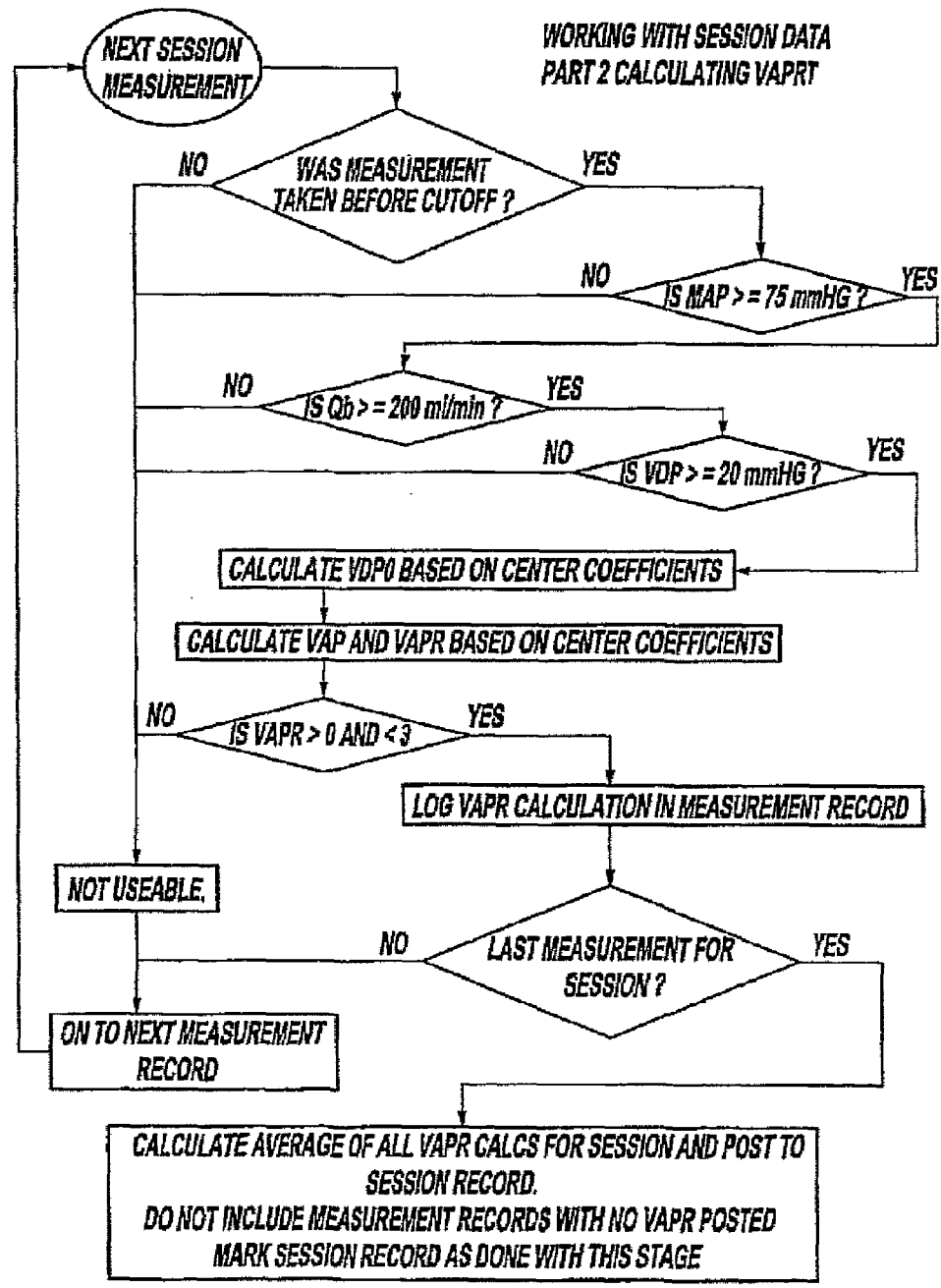
Figure 7C:
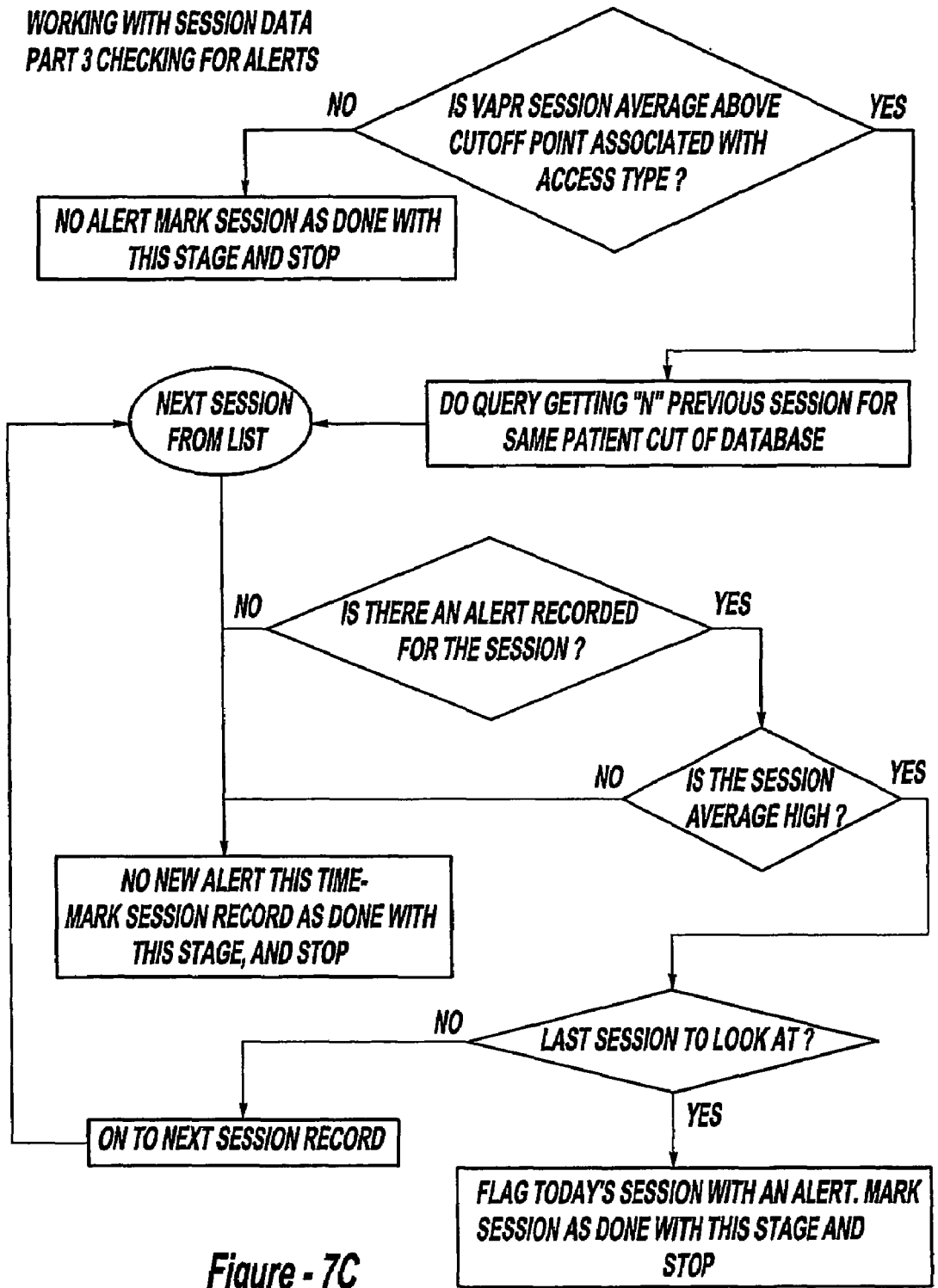
Figure 7D:
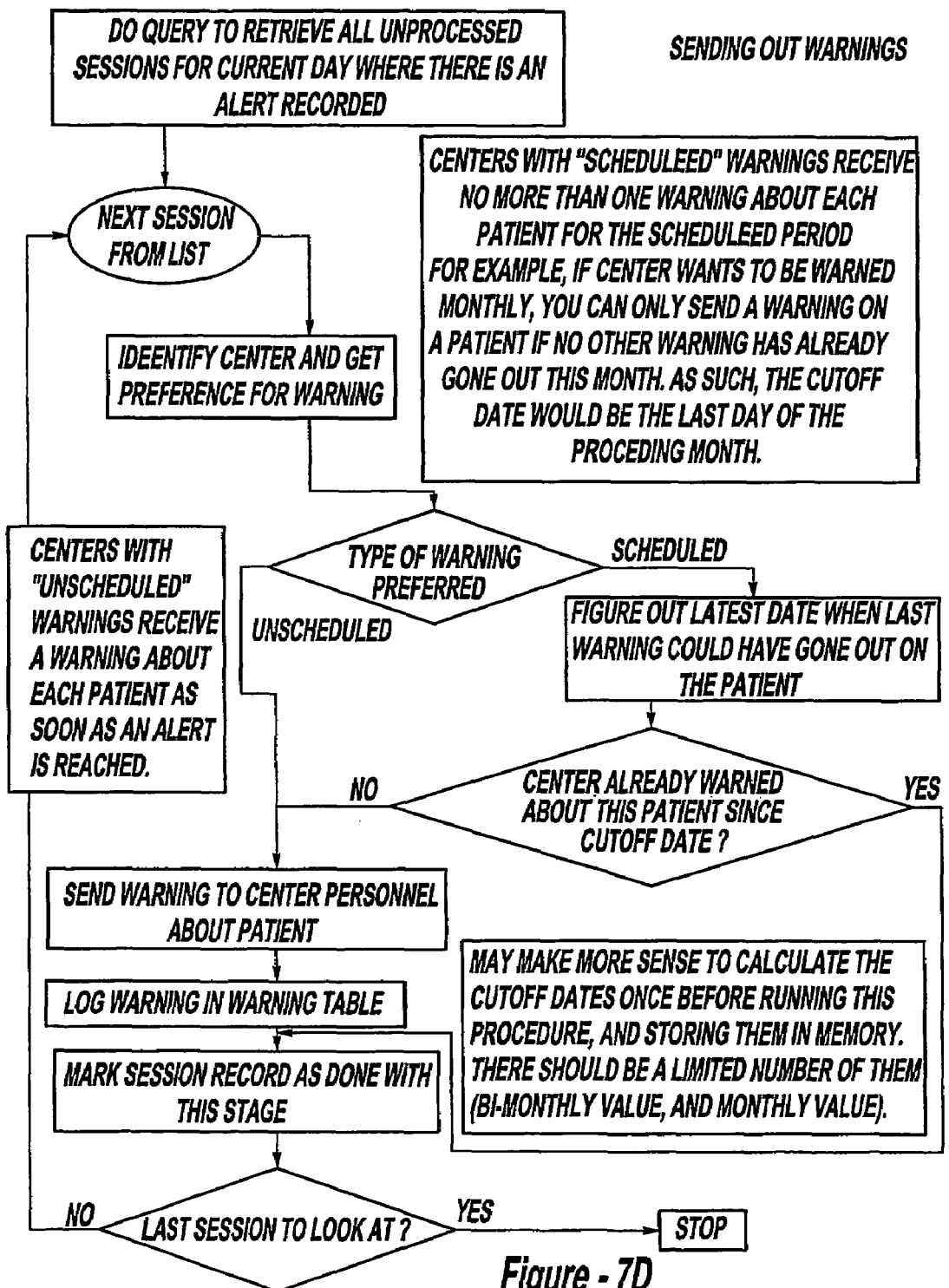
Figure 9A:
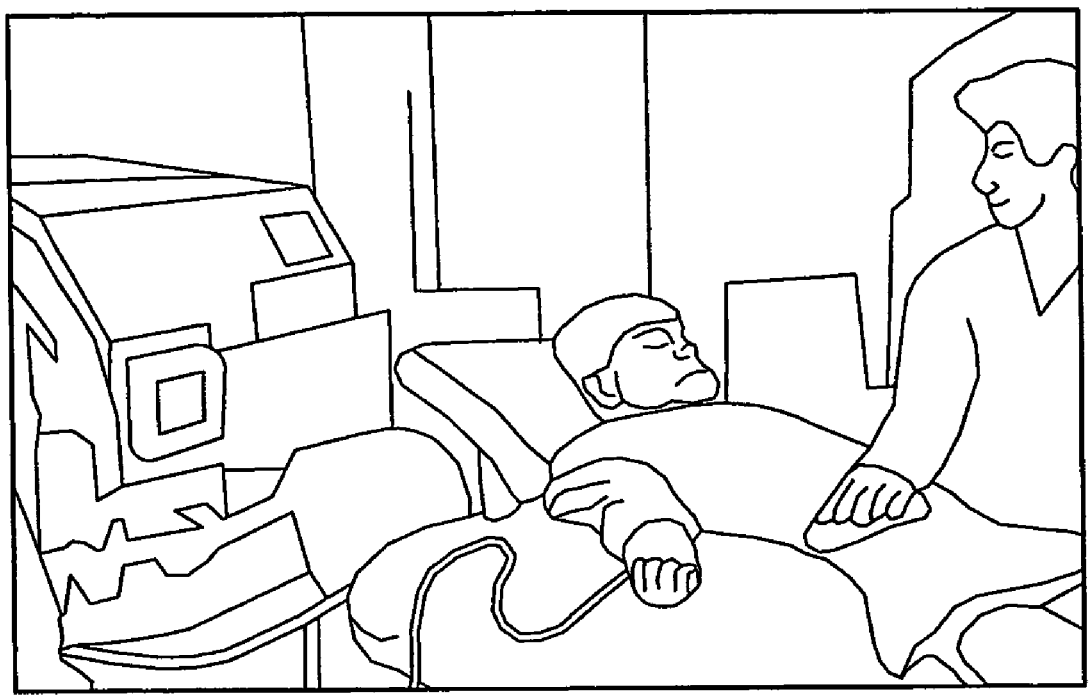
FIGS. 9A and B are photographs depicting dialysis machines for use in conjunction with the device of the present invention.
Figure 9B:
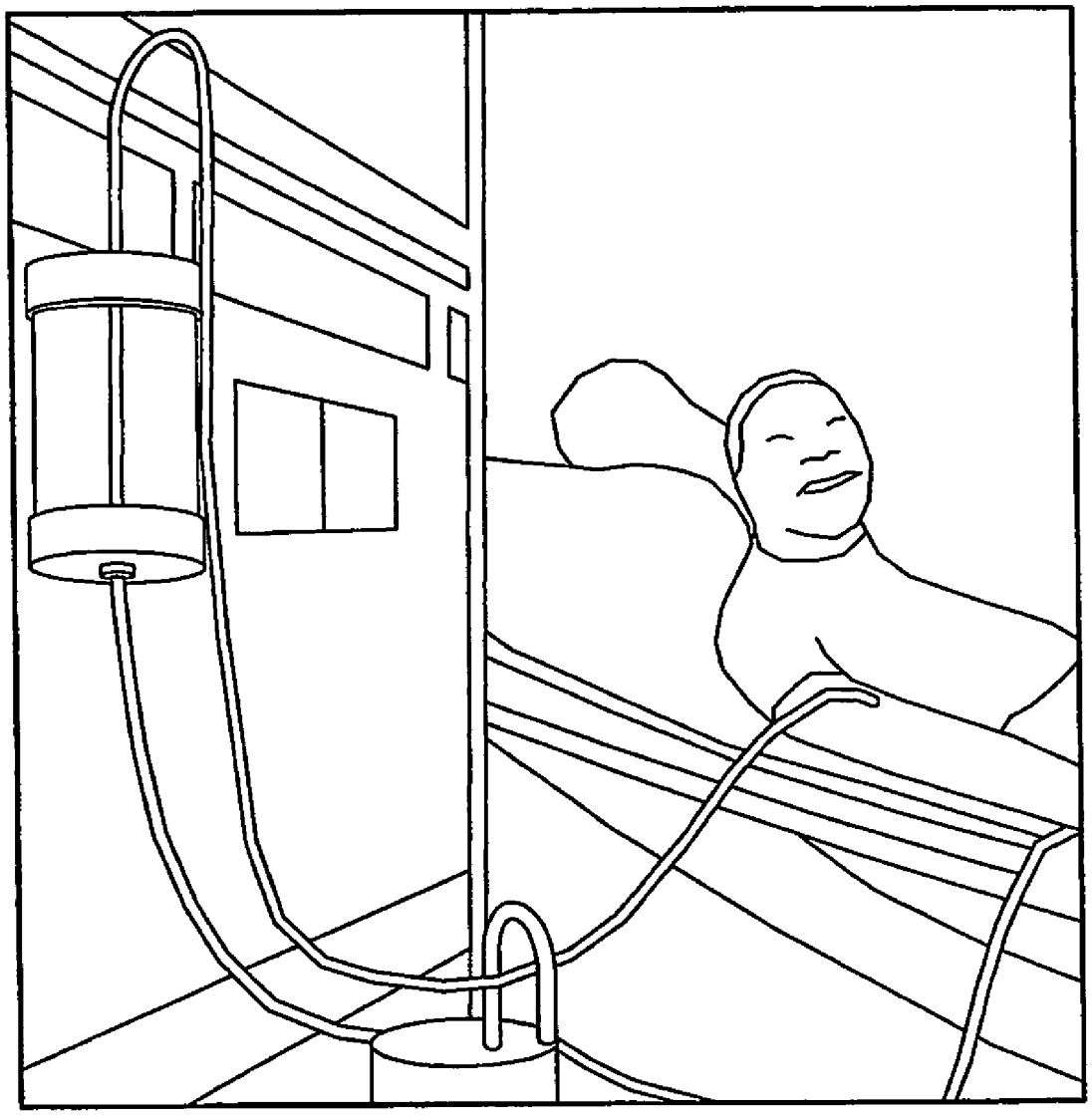

B coefficients were obtained for each hematocrit value. FIG. 6 displays the plot of Coefficient B versus hematocrit and equation (3a) was fit to the data.

$$B = 0.62116 \cdot Hct^2 + 0.01203 \cdot Hct + 0.12754 \qquad \text{Equation (3a)}$$

Equations (2a) and (3a) were combined to yield Equation (4a) that relates $VDP_0$ to Qb and Hct.

$$VDP_0 = 0.00042 \cdot Qb^2 + (0.62116 \cdot Hct^2 + 0.01203 \cdot Hct + 0.12754) \cdot Qb - 17.32509 \qquad \text{Equation (4a)}$$

Equation (4a) was evaluated for accuracy using a nonlinear regression program (DataFit, Oakdale Engineering, Oakdale, Pa., USA). The adjusted coefficient of multiple determination $r^2 = 0.99982$ validated that Equation (4a) represents an accurate mathematical model of the pressure data for access monitoring by dynamic VAPRT.

Application of the Mathematical Model

Analysis of the experimental data for the hemodialysis machine circuit yielded the following second order polynomial equation, henceforth referred to as equation (3):

$$VDP_0 = 0.00042 \cdot Qb^2 + (0.62116 \cdot Hct^2 + 0.01203 \cdot Hct + 0.12754) \cdot Qb - 17.32509 \qquad \text{Equation (3)}$$

The common average intercept, −17.35, was established empirically and is related to the 17 cm difference in height between the needle and drip chamber transducer at Qb=0. When pressure is measured from the transducer proximal to needle, the offset becomes zero, and the relationship between pressure and flow remains curvilinear (FIG. 2, venous needle pressure at Hct=29.1). Thus, $VDP_0$ increases in relationship to increasing Qb and hematocrit.

Equation (3) can be used to calculate $VDP_0$ for any Qb at known Hct. For example, at Qb=500 ml/min and Hct 18.2%, $VDP_0$ is 163 mmHg and increases to 200 mmHg when Hct=38.4%. VAP can be calculated from VDP recorded at HD by Equation (1) and VAPR is calculated by Equation (2). At Hct 38.4%, $Q_b$ 500 ml/min, VDP 265 mmHg, $VDP_0$ 200 mmHg, and MAP 100 mmHg, VAPR=0.65=(265−200)/100. In the case where blood flow (Qb) is equal to zero in equation (3), the following occurs:

$$VDP_0 = 0.00042 \cdot Qb^2 + (0.62116 \cdot Hct^2 + 0.01203 \cdot Hct + 0.12754) \cdot Qb - 17.32509$$

When Qb=0 venous access pressure (VAP) is then calculated using equation (1).

$$VDP_0 = 0 + 0 - 17.32509 = -17.32509$$

$$VAP = VDP - VDP_0 \quad VAP = VDP - (-7.32509) \quad VAP = VDP + 17.32509$$

The constant −17.32509 is determined by the dialysis machine type and the height of the patient's access site. Clinical studies have shown that the venous drip chamber pressure recorded by the machine and corrected for the height difference between the drip chamber transducer the patient's access gives an accurate value for venous access pressure. The algorithm can therefore be incorporated into the dialysis machine. The dialysis machine therefore can automatically take the readings. Additionally, a sensor can be placed on the machine to determine the height difference between the venous drip chamber transducer and the level of the patient's access site.

Receiver Operator Curve (ROC) Evaluation

Patients with grafts (N=117) included during the January 1999 test period and whose data were used for ROC analysis had mean treatment blood flows 438×61 ml/mm, hematocrit 34.0±4.2% MAP 102±14 mmHg, VDP values ranging from 48 to 430 mmHg (mean 214±43 mmHg), and mean VAPR 0.64±0.35.

Figure 3:
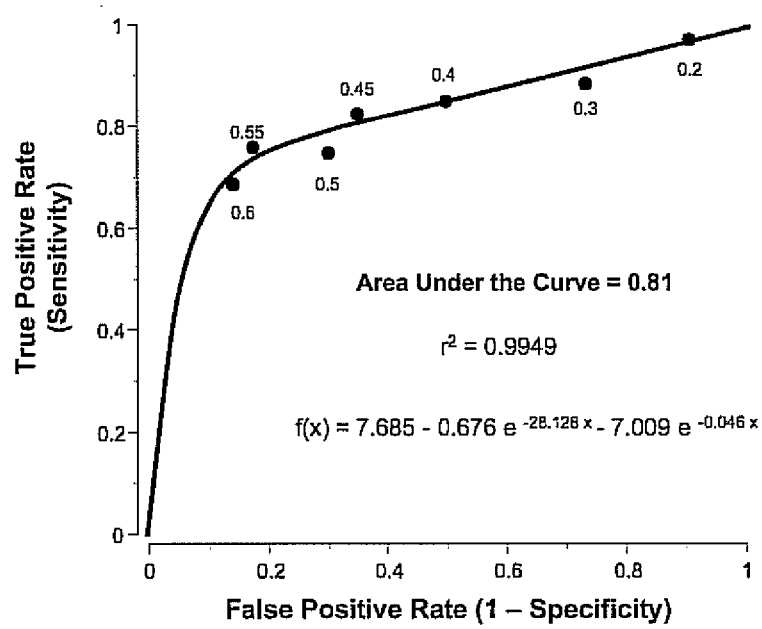
FIG. 3 shows the receiver-operating characteristic (ROC) curves for the January 1999 VAPRT for grafts (117) and fistulas (23) combined and grafts alone, an area of 1 represents an ideal test; an area of 0.5 indicates the test has only a 50% probability determining the correct outcome and an area from 0.80 to 0.90 implies a good test.

The receiver operator curve (ROC) is shown in FIG. 3. The area under the curve corresponds to the probability (0.82) of correctly ranking the two test alternatives, persistence of access patency or occurrence of access failure within six months (16,17). The VAPR cutoff of 0.55 was selected for further clinical testing as it provided a rational compromise between sensitivity (75%) and specificity (83%).

Figure 4:
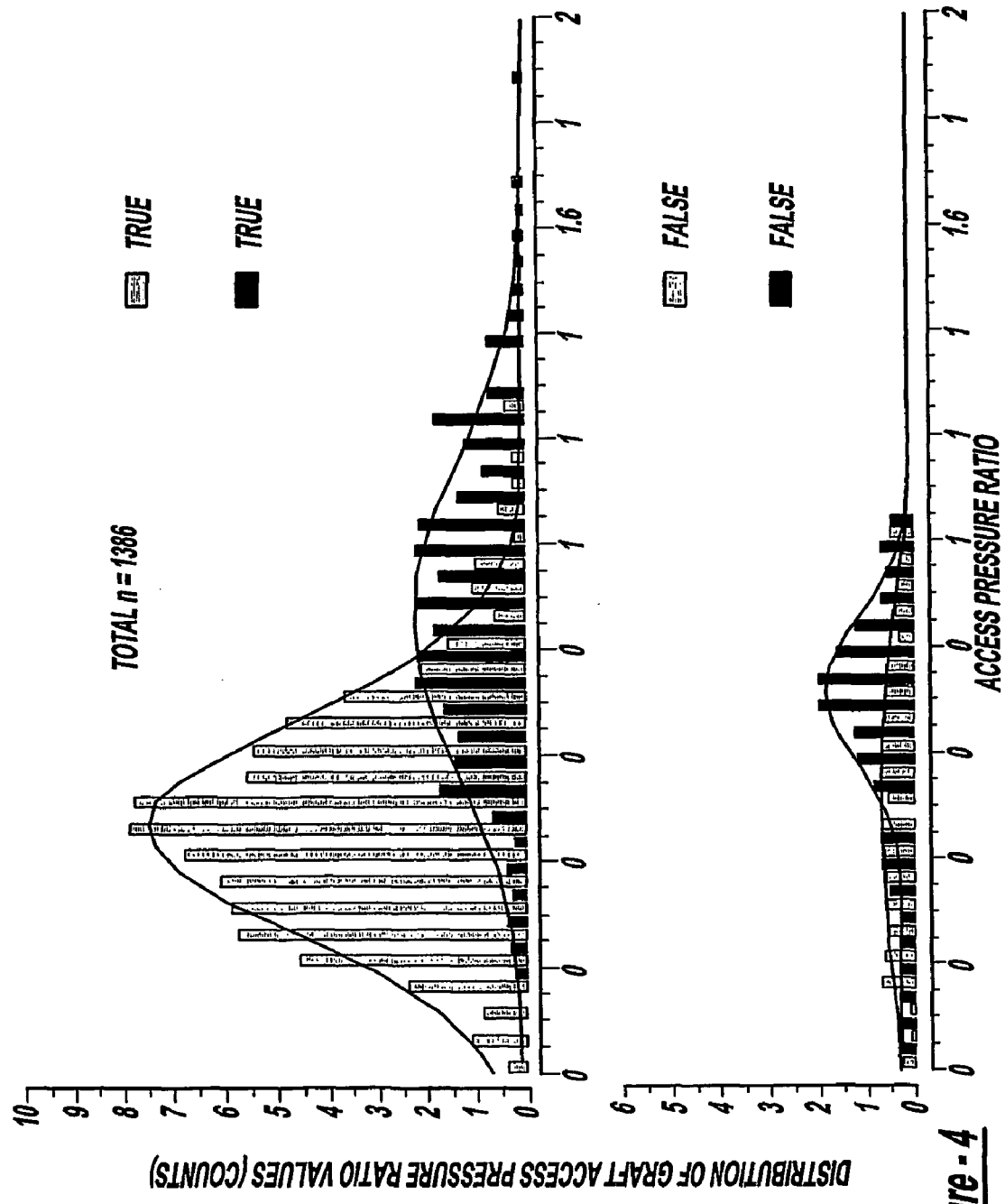
FIG. 4 shows the distribution of access pressure ratio values within the four possible test groups: true positive, true negative, false positive, and false negative for patients with grafts.

FIG. 4 shows the distribution of individual treatment mean VAPR values for all patient observations with grafts in January 1999. The monthly mean VAPR for each patient was calculated from the VAPR values obtained at each treatment. Patients who had a TP test by VAPRT had a median VAPR 0.89 (mean 0.91±0.24). This value was significantly different from the other three possibilities, FP, TN, and FN (Table 1). Patients with TN tests had a median VAPR of 0.48 (mean 0.52±0.15), which differed from FP (median VAPR 0.70, mean 0.70±0 13 P<0.0001) but not from FN (median VAPR 0.57, mean 0.62±0.23). All test groups had VAPR values greater than 1.0, in this case $VDP-VDP_0$ exceeds the mean arterial pressure for the data obtained during treatment and can indicate a problem with needle placement or needle reversal.

Assessment of the VAPRT

Figure 5:
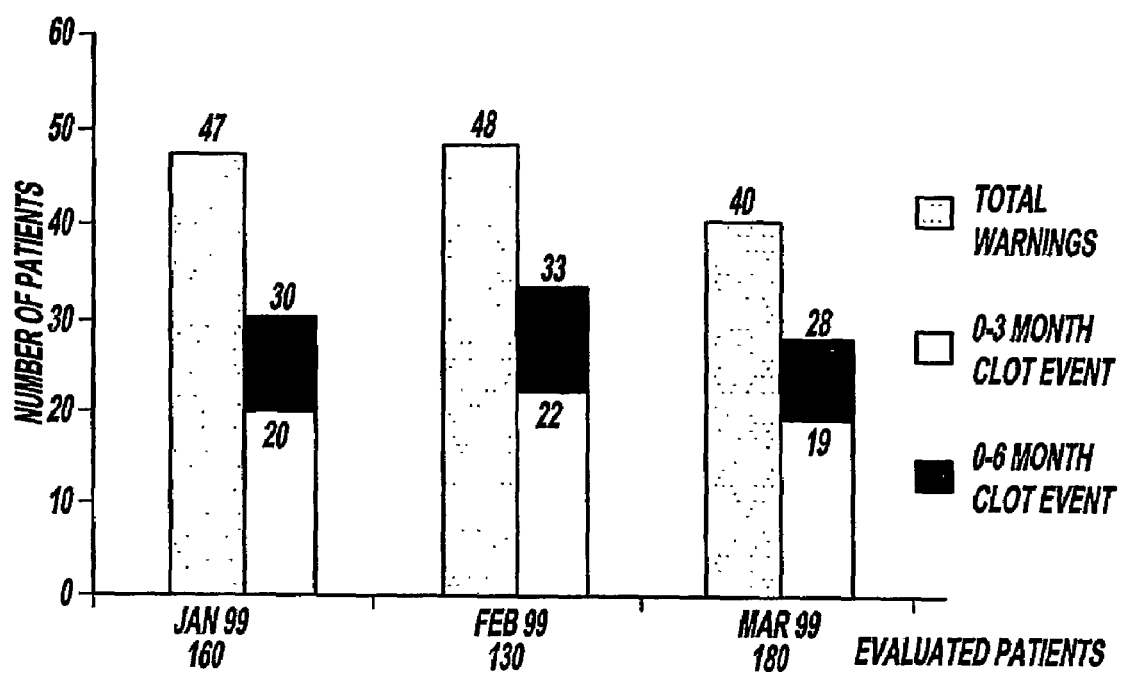
FIG. 5 shows the access pressure ratio test results for three separate months of testing. Patients were followed for six months after each test for an access failure event.

FIG. 5 shows the study results of three months of VAPRT for January, February, and March of 1999. In January 26 out of 112 patients (23%) had a positive VAPRT. During the next three months, thirteen of these patients (50%) experienced access failure, by month six the number increased to nineteen (73%) in the positive test group. For the January test, eight patients that tested negative went on to experience access failure (FN, 7% of population tested). The statistical analysis of the VAPRT are shown in Table 2 and represent the average at three and six months after each test. For the three month follow-up period, the mean test sensitivity of VAPRT was 70±8% while the specificity was 88±2%. These improved to a mean sensitivity of 74±5% and specificity of 96±3% for the six month follow-up period. The VAPRT positive predictive value was 84±10% and the negative predictive value 92±3% for the six month follow-up period.

Discussion

The location of an access stenosis, in part, determines the ability of a monitoring system to detect the lesion. In most grafts, a stenotic lesion develops in the region of the venous anastomosis (10,11,12,13). A stenosis in this region or in the central vein impedes blood flow through the access and increase VAP, which is observed as an increase in VDP. VDP measured during treatment is the sum of three components; the pressure created by blood flowing through the tubing and the needle ($VAP_0$), the static pressure created by the difference in height between the access site and the venous pressure transducer in the dialysis machine and VAP. VDP varies with treatment Qb, VAP, and hematocrit. The difference in height between the access site and the venous pressure transducer also varies,. but, in most cases, does not differ by more than 5 cm from the value of 17 cm used in the model. This results in a ±5.1 mmHg variation in VAP and at MAP=100 mmHg a ±0.05 variation in VAPR. VAP also varies with the MAP and changes in MAP are reflected in VDP. Mapping of the access pressure gradient from the arterial to the venous anastomosis has shown that the slope of the mid graft pressure gradient increases with the development of a stenosis (11). Therefore, VDP increases with increasing distance between the venous needle and venous anastomosis.

Initially it appears that values of VAPR exceeding 1.0 are biologically impossible; however, all tests groups had some VAPR values>1.0, reflecting that physiologically calculated VAP exceeded MAP. For the VAPR data presented in FIG. 4, 9.8% of all values were>1.0, with 27.9% of these in the TP group. Several conditions lead to higher than expected VAPR values. Reversal of arterial and venous needles is probably the most common and occurs in as many as 25% of treatments (18). If a smaller diameter needle is used, without indicating the change in the patient's treatment data, the VAPR values will be falsely elevated. It can also be noted that the small diameter of the venous needle creates turbulent flow in the access that increases resistance to flow through the access. The degree of turbulent flow increases when access flow is reduced due to a venous stenosis and results in increased flow resistance and increased VAP. Lodgment of the venous needle against or partially in the access wall (reduces the needle orifice) or a venous line obstruction produces an increase in the measured VDP and results in episodic high VAPR values. Finally, a difference in MAP in the access extremity from that of the non-access arm that is typically used to monitor blood pressure during hemodialysis (19), which results in an increase in VAPR.

To reduce errors in the VAPRT, patient VAPR values must exceed 0.55 for three consecutive treatments. Initial dynamic access pressure testing developed by Schwab used three consecutive treatments that exceeded predefined limits to indicate a positive test. Dialysis treatments at the end of the month were selected for evaluation because the test results were included in a monthly dialysis patient report and patients may have had an access intervention during the early part of the month. The objective was to maintain a minimal false positive rate to prevent unnecessary further evaluation of the patient's access.

FIG. 2 illustrates the problems that must be resolved when using dynamic measurements of VDP to monitor access pressure. As blood flow increases VDP increases, primarily attributed to augmented resistance created by the venous needle, Elevation of hematocrit also increases VDP. The variability in VDP values from Qb and hematocrit can be reduced if the measurements are made at a fixed, relatively low, blood flow, as demonstrated by Schwab et al (1). However, the appropriate warning level for VDP varies among individuals depending on the MAP and hematocrit. For example with a 15 gauge needle and Qb=200 ml/mm, VDPQ is 33 mmHg at hematocrit 20% and 42 mmHg at hematocrit 36%. Using the criteria that a patient is at risk when the access pressure ratio >0.55, a patient with a MAP of 120 mmHg requires an access pressure >66 mmHg (66/120=0.55) to receive a warning for that treatment. Therefore at Qb=200 ml/mm, the VDP warning level is between 99 (=33+66) mmHg and 108 (=42+66) mmHg for a patient when hematocrit varies between 20% and 36%. Applying the same criteria, a patient with MAP=75 mmHg needs a VDP warning level between 74 and 83 mmHg. It then becomes difficult to select a single VDP warning value for patients at risk for VDP between 74 and 108 mm Hg. By using equation (2) to calculate VAPR, the VAPRT adjusts the VDP warning level for each access pressure measurement in relationship to Qb, hematocrit and MAP. Notably, this absolute pressure range of 74 to 108 mm Hg is significantly lower than that originally reported by Schwab et al (1). The major reason for this difference is needle gauge, 15 gauge for the present invention versus 16 gauge for the Schwab investigation. The component of VDP due to flow through the needle is expected to be significantly greater with a 16 gauge needle (6). Presently, the algorithm is limited to 1 inch 15 gauge needles for cannulation until investigation of other needle gauges has been carried out.

An alternative method of determining the VAPR is to monitor static venous pressures and calculate a static venous access pressure ratio (SVPR) to test for a functionally significant stenosis (8). SVPR is an accurate method for access monitoring, however this method involves training of hemodialysis staff and ongoing monitoring to ensure the validity of the data. The VAPRT does not require specific training and the algorithm examines data currently entered in the patient database and evaluates the patient's access for each dialysis treatment. Finally another method measures static intra-access pressures directly prior to hemodialysis using a hydrophobic filter (22).

A stenosis on the arterial input side of the access or within the access itself is not detected by the VAPRT because this type of lesion reduces access flow and venous access pressure simultaneously. It is feasible to detect an arterial stenosis by developing a model that examines pre-pump arterial drip chamber pressure, (ADP) for values more negative than usual. It is also possible to determine the existence of intra-access lesions if arterial intra-access pressure and VAP can be determined. In this regard, Polaschegg and colleagues (20) described a method for detecting and locating an access stenosis using dynamic arterial and venous access pressure measurements.

Access flow measurements performed within the dialysis unit can determine whether there is a clinically significant reduction of access flow, indicating the necessity for intervention. However, the location of the flow obstruction cannot be definitively identified. The disadvantages of flow measurements are that they require costly equipment, trained personnel and dialysis time for setup and measurement. Studies by Paulson et al. (17,21) indicate that a single access flow measurement is a relatively poor indicator of graft failure. To achieve a sensitivity of 80% for predicting thrombosis requires an unacceptably high FP rate of 58%. The FP rate is so high because the threshold access blood flows that are used to predict graft failure often include many grafts that function at low blood flows, on the other hand, some grafts with good flows inexplicably thrombose without any warning.

Analysis of the data demonstrated that at a sensitivity of 80% the FP rate was 34% for testing grafts. A low FP rate (20% for grafts) was maintained in order not to produce a large number of evaluations that results in interventions by either vascular surgeons or interventional radiologists. It has been suggested that trend analysis can be a better predictor of access failure when using access flow. Trend analysis requires more frequent flow measurements and greatly increases the cost of access flow measurements. The VAPRT calculates a VAPR for each dialysis treatment, rendering it ideal for trend analysis. The current VAPRT models the VAPR trend after the eighth treatment of a month. To minimize spurious alarms, a triplet rule was imposed whereby three consecutive treatments with VAPR>0.55 were necessary to elicit a warning of impending graft failure, and this rule is currently being applied to generate an end-of-month report to assist clinicians in identifying patients with grafts at risk for dysfunction. It is possible to improve the VAPRT test if trend analysis of the all data is included in the algorithm. Greater emphasis can be placed on temporal trends or data filters imposed to exclude clearly erroneous measurements. In addition, analysis of data from two or more consecutive months can increase the power to detect access dysfunction.

The results of this study demonstrate that the VAPRT is a useful noninvasive screening test that identifies a population of dialysis patients that is at risk for access failure. The key component in implementing this system is computer access to the required treatment and laboratory data. The software algorithm to analyze hemodialysis data is incorporated as a standard end-of-month report and as an Internet-based accessible vascular access monitoring system. All patients exhibiting a warning status are flagged and a database trigger is available on-demand to create a report for any location or time period. Access intervention can be tracked along with warning status, thus permitting immediate follow-up and timely cost-saving interventions.

Example 2

An alternative method is provided for measuring access pressure through a access needle that is flow-connected to the vascular system of a patient. The method comprises the steps of: connecting one end of pressure tubing to the outer end of the access needle tubing, with a membrane blocking the flow of blood while permitting the passage of air through to a pressure gauge. The membrane suppresses or dampens the pressure pulses or oscillations through the tubing. Thus, upon opening the access needle tubing to the vascular system, blood flowing into the tubing compresses the air in the pressure tubing, plus the connected gauge, causing pressure from the vascular system to be readable by the gauge while the pressure pulses are attenuated in a simple, nonelectronic manner.

Preferably, the "membrane" mentioned above is a microporous membrane, typically a microporous block or plug positioned within or adjacent to the pressure tubing and capable of providing the damping or attenuation of the pulsatile nature of the pressure from the patient's cardiovascular system at the gauge.

Preferably, the internal volume of the pressure tubing is less than the internal volume of the access needle tubing. As the result of this, pressurized blood entering the empty access needle tubing as the pressure is read does not advance completely to the level of the membrane, but is halted by compression of the initial air in the tubing, as well as the residual volume of air within the pressure gauge. This can be accomplished by providing pressure tubing that has a connector at each end, the tubing having a single lumen of reduced diameter from normal flexible tubing, which lumen diameter is typically no more than about one third of the outer diameter of the tubing. Thus, the internal volume of the pressure tubing can be less than the internal volume of the first tube even if the length of the pressure tubing is greater than the length of the first tube, this situation is preferred so that there is adequate tube length to conveniently hold a pressure gauge and to position it at approximately the level of the patient's heart and to read it with ease, and also to reduce the chance that the access needle connection to the patient's access is disturbed as the pressure gauge is connected and handled.

Preferably, the set that defines the pressure tubing carries a microporous member that is capable of preventing the passage of bacteria therethrough. This can be a second microporous member if desired, above and beyond the microporous plug described above that suppresses pressure oscillations through the pressure tubing, thus attenuating the pressure pulses. A conventional 0.2 micron bacterial filter can be used. This uniquely provides both flow blocking and aseptic conditions with commercially available materials.

Alternatively, the microporous member can be a plug that has a bacteria blocking capability similar to conventional 0.2 micron bacterial filters. Also, a membrane-type bacterial filter can have pores that are small enough to provide the desired attenuation of pressure pulses through the pressure tubing, to facilitate reading of the gauge.

Also, if desired, the pressure tubing can have a bore that is sufficiently narrow and of a length to provide the desired pressure pulse attenuation through the tubing without the need for a porous plug so that, typically, only a bacteria blocking filter membrane is provided, as needed, to protect the patient from bacterial contamination through connection to a nonsterile pressure gauge.

Further development of the device includes replacement of the pressure gauge with a handheld microprocessor controlled device that measures and records the pressure measurements. An algorithm in the device calculates the average pressure over a predetermined sampling period. The device also contains a computer database to recall individual patient information and to record current pressure measurements in the patient's database record. Data from the device can be transferred via a communication port to a larger computer system with a more extensive patient database.

Example 3

This example demonstrates the case where blood flow (Qb) is equal to zero in equation (3). The constant term (−17.32509 in equation 3) needed to correct for the difference in height between the venous drip chamber and the level of the patient's access site was calculated for three different dialysis machines and clinical data was evaluated to demonstrate the effectiveness of the system.

The measurement of venous intra-access pressure (VAP) normalized by mean arterial blood pressure (MAP) facilitates detect venous outlet stenosis and correlates with access blood flow. General use of VAP/MAP is limited by time and special equipment costs. Bernoulli's equation relates differences between VAP (recorded by an external transducer as PT) and the venous drip chamber pressure (VDP) at zero blood pump flow, the difference in height ($\Delta H$) between the measuring sites and fluid density determine the pressure due to the difference in height $\Delta PH=VAP-VDP$. They were therefore correlated VDP and PT measurements at six different dialysis units each using one of three different dialysis machines. Both dynamic (i.e. with blood flow) pressures and static pressures were measured. Validation studies showed that changes in mean blood pressure, zero calibration errors, and hydrostatic height between the transducer and drip chamber accounted for 90% of the variance in VDP with $\Delta PH=-1.6+0.74\cdot\Delta H$ ($r=0.88$, $p<0.001$). The major determinant of static VAP/MAP was access type and venous outflow problems. In grafts, flow averaged $555\pm45$ mL/min for VAP/MAP>0.5 and $1229\pm112$ mL/min for VAP/MAP<0.5. $\Delta PH$ varied from 9.4 to 17.4 mm Hg among the six centers and was related to $\Delta H$ between the drip chamber and the arm rest of the dialysis chair. Concordance between the values of VAP/MAP calculated from PT and from VDP+PH was excellent. It was concluded that static VDP measurements corrected by an appropriate $\Delta PH$ can be used to prospectively monitor prosthetic bridge grafts for stenosis.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the described invention, the invention can be practiced otherwise than as specifically described.

TABLE 1

Comparison of Monthly Mean Graft VAPR Values for the Different Test Groups

|  | Count | Mean | Std. Dev. | Std. Err |
|---|---|---|---|---|
| True Positive | 27 | 0.909 | 0.237 | 0.046 |
| True Negative | 67 | 0.515 | 0.149 | 0.018 |
| False Negative | 9 | 0.616 | 0.215 | 0.072 |
| False Positive | 14 | 0.698 | 0.125 | 0.033 |

|  | Mean Difference | p-Value |
|---|---|---|
| True Positive, True Negative | 0.394 | <0.0001 |
| True Positive, False Negative | 0.293 | 0.0024 |
| True Positive, False Positive | 0.211 | 0.0036 |
| True Negative, False Positive | −0.183 | <0.0001 |
| True Negative, False Negative | −0.102 | 0.0734 |
| False Positive, False Negative | 0.082 | 0.2595 |

TABLE 2

Statistical Analysis of Venous Access Pressure Ratio Test for Grafts Showing Mean Values for Three Months of Testing

|  | Test Period | |
|---|---|---|
|  | 0-3 mo | 0-6 mo |
| Sensitivity (%) | 70 ± 8 | 74 ± 5 |
| Specificity (%) | 88 ± 2 | 96 ± 3 |
| Positive Predictive Value (%) | 52 ± 10 | 84 ± 10 |
| Negative Predictive Value (%) | 94 ± 2 | 92 ± 3 |
| False Positive rate (%) | 12 ± 2 | 4 ± 3 |

REFERENCES

1. Schwab S J, Raymond F R, Saeed M, Newman G E, Dennis P A, Bollinger R R: Prevention of hemodialysis fistula thrombosis. Early detection of venous stenosis. Kidney Int 36:707-711, 1989.
2. Strauch B S, O'Connell R S, Geoly K L: Forecasting thromboses of vascular access with Doppler color flow imaging. Am J Kidney Dis 19:554-557, 1992.
3. Levy S S, Sherman R A, Nosher J L: Value of clinical screening or detection of asymptomatic hemodialysis vascular access stenoses. Angiology 43:421-424, 1992.
4. Van Stone J C, Jones M, Van Stone J: Detection of hemodialysis access outlet stenosis by measuring outlet resistance. Am J Kidney Dis 23:562-568, 1994.

5. Rehman S U, Pupim L B, Shyr Y, Hakim R, Ikizier T A: Intradialytic serial vascular access flow measurements. Am J Kidney Dis 34:471-477, 1999.
6. Besarab A, Sullivan K L, Ross R, Moritz M: The utility of intra-access monitoring in detecting and correcting venous outlet stenoses prior to thrombosis. Kidney Int. 47:1364-1373, 1995.
7. Koksoy C, Kuzu A, Erden I, Turkcapar A G, Duzgun I, Anadol E: Predictive value of color Doppler ultrasonography in detecting failure of vascular access grafts. Brit J Surg 82:50-55, 1995.
8. Besarab A, Al-Saghir F, Alnabhan N. Lubkowski T, Frinak 5: Simplified measurement of intra-access pressure. ASAIO J 42:M682-M687, 1996.
9. Sands J J, Miranda C L: Prolongation of hemodialysis access survival with elective revision. Clin Nephrol 44:334-337, 1995.
10. Palder S B, Kirkman R L, Whittemore A D, Hakim R M, Lazarus J M, Tilney N L: Vascular access for hemodialysis. Patency rates and results of revision. Ann Surg. 202:235-239,1985.
11. Sullivan K L, Besarab A, Bonn J, Shapiro M J, Gardiner G A, Moritz M J: Hemodynamics of failing dialysis grafts. Radiology 186:867-872, 1993.
12. Beathard G A, Percutaneous transvenous angioplasty in the treatment of vascular access stenosis. Kidney International. 42(6):1390-7, 1992.
13. Kanterman R Y, Vesely T M, Pilgram T K, Guy B W, Windus D W, Picus D: Dialysis access grafts: anatomic location of venous stenosis and results of angioplasty. Radiology. 195(1):135-9, 1995.
14. Besarab A, Dorrell 5, Moritz M, Michael H, Sullivan K: Determinants of measured dialysis venous pressure and its relationship to true intra-access venous pressure. Trans Am Soc Artif Intern Organs 37:M270-M271,1991.
15. Sparks S R, VanderLinden J L, Gnanadev D A, Smith J W, Bunt T J: Superior patency of perforating antecubital vein arteriovenous fistulae for hemodialysis. Annals of Vascular Surgery. 11(2):165-7, 1997.
16. Metz C E: Basic principles of ROC analysis. Semin Nuclear Med. 8:283-98, 1978.
17. Paulson W D, Ram S J, Birk C G, Work J: Does blood flow accurately predict thrombosis or failure of hemodialysis synthetic grafts? A meta-analysis. Am J Kidney Dis 34(3): 478-85, 1999.
18. Shapiro W, Gurevich L: Inadvertent reversal of hemodialysis lines—A possible cause of decreased hemodialysis efficiency. [Abstract] J Am Soc Nephrol 8:172A, 1997.
19. Besarab A, Lubkowski T, Yu A, Frinak S. Determinants of vascular access flow. ASAIO J 47(5):501-506, 2001.
20. Polaschegg H D, Techert F, Wizemann V: Dynamic pressure measurement for detection of blood access stenosis. Edtna-Erca J 24(4):39-44, 1998.
21. Paulson W D, Ram S J, Birk C G, Zapczynski M, Martin S R, Work J: Accuracy of decrease in blood flow in predicting hemodialysis graft thrombosis. Am J Kidney Dis 35(6): 1089-1095, 2000.
22. Besarab A, Lubkowski T, Frinak 5: A simpler method for measuring intra-access pressure. J Am Soc Nephrol. 11:202A, 1999.

What is claimed is:

1. A detection device for detecting intravascular pressure in a person, said device comprising:
    analyzing means for automatically deriving venous access pressure (VAP) in proximity of a suspected location of a blood flow restriction and determining a ratio of VAP to mean arterial pressure, where analyzing means determines multiple VAP values over multiple time periods and determines multiple ratios, one for each VAP value, and
    detecting means for comparing each ratio to a standard ratio, where the detecting means detects the blood flow restriction only when elevation of the ratio above the standard ratio over a series of consecutive comparisons is indicated.

2. The device according to claim 1, wherein said analyzing means includes a microprocessor.

3. A system for providing warning of potential health problems due to irregular intravascular pressure caused by blockage of the blood vessels in proximity of an extracorporeal blood access, said system comprising: a detection device according to claim 1; and communication means operably connected to said device for communicating a warning when said device detects the blood flow restriction.

4. The system according to claims 3, wherein said communication means is selected from the group consisting essentially of electronic communications, facsimile, telephone, cable modem, and T1 connection.

5. The device according to claim 1, wherein said device is a blood pressure detection device.

6. The device according to claim 1, wherein said blood flow restriction indicates a risk selected from the group consisting of potential access failure, heart attack, and stenosis.

7. The device according to claim 1, wherein the analyzing means derives the venous access pressure from a venous drip pressure measurement.

8. A method of detecting potentially compromised or restricted blood flow by:
    calculating a ratio of venous access pressure to mean arterial pressure, where the venous access pressure is in proximity of a suspected location of the compromised or restricted blood flow;
    using an analyzer, comparing the ratio to a standard;
    repeating the calculating and comparing steps;
    detecting restricted blood flow only when elevation of the ratio above the standard over a series of consecutive comparisons is indicated.

9. The method of claim 8, wherein said comparing step further includes automatically comparing the ratio to the standard.

10. The method of claim 9, wherein said automatically comparing step further includes automatically comparing the ratio to the standard using an algorithm.

11. The method of claim 8, wherein said calculating step further includes automatically calculating the ratio.

12. The method of claim 8, wherein said calculating step further includes automatically calculating the ratio during a procedure.

* * * * *